United States Patent [19]

Emeury et al.

[11] 4,211,874
[45] Jul. 8, 1980

[54] CONTINUOUS PROCESS FOR THE MANUFACTURE OF DINITROGLYCOLURILE

[75] Inventors: Jean-Marie L. Emeury, Sorgues; Hubert H. Girardon, Villeneuve les Avignon, both of France

[73] Assignee: Societe Nationale des Poudres et Explosifs, Paris, France

[21] Appl. No.: 46,190

[22] Filed: Jun. 6, 1979

[30] Foreign Application Priority Data

Jun. 23, 1978 [FR] France .............................. 78 18785

[51] Int. Cl.$^2$ ........................................... C07D 487/04
[52] U.S. Cl. ..................................... 548/304; 149/92
[58] Field of Search ......................................... 548/304

[56] References Cited

FOREIGN PATENT DOCUMENTS 2435651 2/1975 Fed. Rep. of Germany ........... 548/304
2238703 2/1975 France .................................... 548/304

OTHER PUBLICATIONS

Bouleau et al., Chem. Abst. 1977, vol. 86, No. 86:75499d.

Franchimont et al., Recueil des Travaux Chimiques des Pays-Bas, 1888, vol. 7, pp. 12–24.

*Primary Examiner*—Natalie Trousof
*Attorney, Agent, or Firm*—Bucknam and Archer

[57] ABSTRACT

The invention relates to a continuous process for the manufacture of dinitroglycolurile by nitrating glycolurile with absolute nitric acid.

According to the invention, the nitration is carried out in at least two reactors in a cascade, a homogeneous phase being produced in the first reactor and a heterogeneous phase being produced in the second reactor.

An initial nitration ratio of between 3.5 and 9 is preferably used and a temperature of between 30° and 40° C. and between 45° and 70° C. is preferably caused to prevail in the first and the second reactor respectively. If desired, at least one third reactor can be used, in which the reaction mixture is brought back to ambient temperature.

Application: production of the secondary explosive DINGU, having improved stability in the crude form, with an excellent yield.

4 Claims, No Drawings

CONTINUOUS PROCESS FOR THE MANUFACTURE OF DINITROGLYCOLURILE

The present invention relates to a continuous process for the preparation of dinitroglycolurile.

Dinitroglycolurile was first synthesised by FRANCHIMONT and KLOBBIE (Recueil des Travaux Chimiques des Pays Bas, Volume 7, page 18) in 1888. These authors initially assigned an obviously incorrect formula to the product which they had obtained by dissolving one part by weight of glycolurile in five parts by weight of absolute nitric acid, and then put forward the hypothesis (Op. cit., pages 246-247) that the dinitroglycolurile resulting from this operation must have the formula:

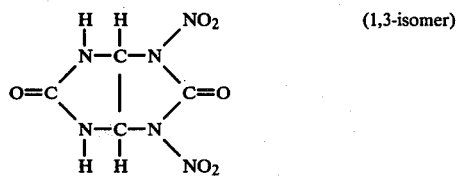
(1,3-isomer)

because of the nature of the products resulting from the decomposition of the compound, carried out in boiling water.

However, it is quite clear that two other isomers, of the formulae:

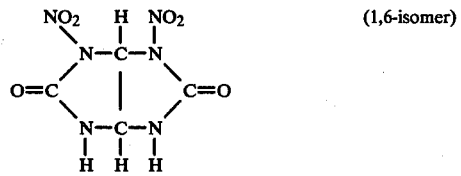
(1,6-isomer)

and

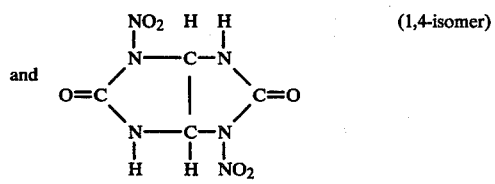
(1,4-isomer)

can be formed.

A long time after dinitroglycolurile and its isomers had fallen into oblivion, the Applicant Company demonstrated, in her French Pat. No. 2,238,703, the value of this compound as a secondary explosive and then, in her French Patent Application No. 77/03,392, as an energy-producing additive considerably improving the properties of the hexolites or "B" compositions.

There is therefore a great demand for a process for the mass production of dinitroglycolurile (or DINGU) which can be used as an explosive. Advantageously, a process of this kind should be continuous.

If the process described by FRANCHIMONT and KLOBBIE (Op. cit.) is applied, a large proportion of the 1,3-isomer of DINGU, which can be decomposed by boiling water, is formed. Now, this isomer is substantially less stable than the other two isomers (1,4 and 1,6), with the result that, for certain applications, it is necessary to subject the crude reaction product to a treatment with boiling water so that only the stable isomers of DINGU are recovered. As a result, there is a very substantial reduction in the overall yield of the nitration.

On the other hand, the presence of this homogeneous phase seemed to be extremely favourable for the kinetics of the glycolurile nitration reaction, taking all the isomers into account.

Confronted with these previously undisclosed and surprising observations, the Applicant Company has now found a process for the manufacture of DINGU, which operates continuously and favours the formation of the most stable isomers of DINGU.

The process according to the invention consists in carrying out the synthesis of dinitroglycolurile by nitrating glycolurile with absolute nitric acid and is characterized in that the nitration is carried out continuously and in a cascade, a homogeneous liquid phase being produced by simultaneously and continuously introducing glycolurile and absolute nitric acid into a first stirred reactor, and a heterogeneous phase then being produced in a second stirred reactor.

The success of the process depends essentially on observing the characteristic conditions which have just been mentioned. However, the Applicant Company has also found that more restrictive working conditions exist which lead to a particularly advantageous operation. Two factors of great importance are the initial nitration ratio and the temperature prevailing in the two stages of the cascade.

According to a first preferred embodiment of the process according to the invention, an initial nitration ratio of between 4 and 8, and preferably between 5 and 7, is used. The initial nitration ratio is understood as meaning the ratio of the masses of absolute nitric acid and glycolurile introduced into the first reactor per unit time. The nitric acid used within the scope of the present process must be absolute, that is to say it must contain from 95 to 100% by weight of $HNO_3$.

According to a second variant of the process according to the invention, a temperature of between 25° and 50° C., and preferably between 30° and 40° C., is caused to prevail in the first reactor. In the second reactor, a temperature of between 45° and 70° C., and preferably between 50° and 65° C., is caused to prevail. Above 70° C., the nitration reaction is admittedly possible, but is accompanied by oxidation phenomena. Below 45° C., the nitration reaction in the heterogeneous phase is relatively slow, which unnecessarily increases the residence time in the reactor and the size of the latter, and this is not desirable for reasons of safety and viability.

According to a third variant of the process, the first two reactors in a cascade, which have been mentioned above, are followed by at least one third stirred reactor in which the temperature of the reaction mixture is brought back to about ambient temperature and in which the nitration is completed if necessary. According to the first variant, the reaction mixture is finally filtered and the resulting crystalline mass is washed until the washings are neutral, optionally cleared and dried. The washing until the washings are neutral can be carried out with cold water until a pH of 5 is obtained, the optional clearing operation can be carried out with methanol or ethanol and the drying can be carried out at about 65° C. If the present variant is not used, the reaction mixture is not discharged in a cascade into the third reactor but onto a hot filter in which the filtered product is subjected to the treatment which has just been described, preferably after cooling.

Although the process according to the invention makes it possible considerably to reduce the production, in the final reaction mixture, of products of low stability (probably the 1,3-isomer of DINGU), the filtered product, or the filtered, washed and optionally cleared product, can, if desired, be subjected to washing with boiling water.

Finally, in the foregoing text, it has been specified that the two or three reactors, arranged in a cascade according to the process of the invention, are stirred. The stirring in the first reactor must be sufficient to enable a rapid dissolution of the glycolurile in the simultaneously introduced nitric acid or in the reaction mixture which is already present in the reactor. In the second reactor, the stirring must be sufficient to keep the crystalline suspension of DINGU in motion in the liquid reaction mixture; if a nitration ratio of less than 5 is chosen, vigorous stirring is generally necessary in order to achieve the abovementioned conditions. Finally, in the last reactor, which is optional, the stirring is advantageously similar to that being carried out in the second reactor, this optionally also permitting the emptying of the said reactor, through an overflow, as it fills up.

The starting or stopping of an installation employing the process according to the invention does not present any particular difficulties. When starting, it is possible, for example, to totally fill the first reactor and half fill the second reactor with absolute nitric acid. When stopping the installation, it suffices to cut off the feeds of fresh reactants, to bring the first two reactors to the temperature required for the second reactor under normal working conditions, to allow the contents of the said two reactors to age, and finally to discharge these contents onto a filter.

As regards the residence times in the first two reactors, they are adjusted, according to the invention, so that a homogeneous phase is present in the first reactor and a heterogeneous phase is present in the second reactor.

It is to be noted that the present process could use fuming nitric acid, that is to say 100% strength nitric acid to which $N_2O_5$ has been added. However, there would be no unexpected advantage in following this procedure; on the contrary, there would be the risk of the formation of SORGUYL (tetranitroglycolurile) which would finally be hydrolysed during the final washing with water or the final treatment with boiling water.

The yield of the process according to the invention is between 75 and 95%, which is at least comparable to the yield of the conventional discontinuous process in the homogeneous phase. On the other hand, the crude reaction product, which has been filtered, washed with cold water, cleared with alcohol and then dried, generally contains more than 12% of nitrogen and contains less than 5% by weight of unstable derivatives which can be hydrolysed with hot water, whereas, when operating solely in the homogeneous phase (discontinuously or continuously), at least 10% of hazardous unstable derivatives are obtained; in fact, although the product obtained by the process according to the invention has an excellent stability in vacuo (less than 2 cm$^3$ of gases evolved per gram of DINGU after 100 hours at 130° C.), the same cannot be said for the product obtained in the homogeneous phase (more than 15 cm$^3$/g in 24 hours at 130° C.).

The following examples are given by way of a non-limiting illustration of the process according to the invention; a comparison of the conventional process in the homogeneous phase, which has been made continuous in a previously undisclosed manner, with the process according to the invention will also be found therein.

EXAMPLE 1: Process according to the invention

Three reactors, having respective useful volumes of 170, 500 and 330 ml and arranged in a cascade, were used. These reactors were equipped with a concentric tube permitting both the passage of the stirrer arm and the introduction either of the reactants (in the case of the first reactor) or of the reaction mixture being discharged from the preceding reactor (in the cases of the second and third reactors). Thus, the reaction mixture was introduced through the centre of the reactor and, after stirring, rose up the walls of the reactor as far as an orifice through which it was discharged either into the next reactor (in the case of the first and second reactors) or onto a filter (in the case of the third reactor).

A solids dispenser, consisting of a hopper in the shape of a truncated cone, the base of which possessed an orifice opening out onto a alveolate axle driven by an electric motor, made it possible to ensure a flow rate of 200 g/hour of glycolurile. The absolute nitric acid (98% strength) was introduced at the rate of 1,200 g/hour, this being a nitration ratio of 6.

It was found suitable to fix the stirring at 500 rpm in each reactor, in order to ensure the rapid production of a homogeneous mixture in the first reactor. Keeping the suspension of crystals of DINGU in motion in the second and the third reactor was achieved by gradually increasing the stirring from 500 rpm to 850–900 rpm (cruising speed).

The temperature prevailing in the first reactor fluctuated between 30° and 40° C. Those prevailing in the second and third reactors were fixed at 70° and 25° C. respectively.

The residence times in the three reactors were 10, 30 and 20 minutes respectively.

The installation operated for several hours, after which the mean yield of crude DINGU was found to be equal to 90%.

The reaction product, which was filtered, then washed with cold water until washing waters of pH 5 were obtained, then cleared with methanol and finally dried at 65° C., had a purity of 95.5%. Its stability in vacuo was 1.4 cm$^3$ of gases evolved per gram in 100 hours at 130° C. and the nitrogen content was 11.99%. When treated with boiling water, this dingu lost only 4% of its weight and its stability in vacuo was not seen to improve substantially.

EXAMPLE 2: Conventional process applied continuously

The process of FRANCHIMONT and KLOBBIE was operated continuously in a previously undisclosed manner. 200 g/hour of glycolurile and 2,000 g/hour of 98.8% strength nitric acid were introduced into a reactor having a useful volume of 1.4 liters, which reactor was analogous in principle to one of those of Example 1, that is to say it permitted the continuous introduction of the reactants, the stirring of the mixture thereof and the continuous discharging of the reaction product through an overflow. With a residence time of 60 minutes and the stirring fixed at 500 rpm, a homogeneous effluent reaction mixture was obtained. The temperature in the reactor was kept at 55° C. The discharged reaction mixture was received in ice-cooled water in a crystalliser. The precipitate, which was rather slow to form, was collected on a filter and then washed with water until the pH of the washings was 5, cleared with methanol and dried at 65° C.

Crude DINGU was obtained with a yield of 83.6%. This DINGU had a nitrogen content of 11.8% and a stability in vacuo of 15 cm$^3$/g in 24 hours at 130° C.

When treated with boiling water, the DINGU obtained by this process loses 20% of its weight; on the other hand, the resulting product has a stability in vacuo of 2.5 cm$^3$/g in 100 hours at 130° C.

It is therefore seen that the process according to the invention makes it possible to obtain stable DINGU with a better yield than the process derived from the prior art, whilst permitting the economy of a hot hydrolysis operation.

EXAMPLE 3: Process according to the invention on a semi-industrial scale

Three nitrators in a cascade, respectively having a nominal volume of 60 liters and a useful volume of 50 liters, were used; 15 kg/hour of glycolurile were introduced with the aid of a "DOSAPRO" screw-type metering device. The nitric acid (98.8% of HNO$_2$) was introduced at the rate of 90 kg/hour and the nitration ratio was approximately equal to 6.

The temperatures prevailing in the reactors were 30°–40° C. (variable), 66±1° C. and 20±2° C. respectively. These temperatures were easily maintained by circulating water at 30° C. and at 76° C., respectively, in the double envelope of the first and the second nitrator, and circulating brine at −10° C. in the double envelope of the third nitrator.

The total duration of the operation was 10 hours. Initially, the first reactor was totally filled and the second was half filled with 98.8% strength nitric acid. At the end of the operation, the first nitrator was heated at 66±1° C. for one hour, as was the second nitrator; the content of the three reactors was finally discharged onto a filter.

The crude DINGU from synthesis was washed until the pH of the washing waters was 6. A total of 313 kg of DINGU having a moisture content of 28.7%, that is to say 223 kg of dry DINGU, was finally collected. The yield of the nitration was therefore 91%.

A 500 g sample of this DINGU was washed with boiling water; 477.5 g of DINGU, possessing an excellent stability in vacuo of 0.89 cm$^3$/g in 130 hours at 100° C., were finally collected. The nitrogen content of this product was 12.11% (theory: 12.06%). It is deduced therefrom that the crude reaction DINGU contained less than 5% by weight of unstable glycolurile nitration products which could be hydrolysed in hot water.

We claim:

1. Process for the manufacture of dinitroglycolurile by nitrating glycolurile with absolute nitric acid, characterised in that the nitration is carried out continuously and in a cascade, a homogeneous liquid phase being produced by simultaneously and continuously introducing glycolurile and absolute nitric acid into a first stirred reactor, and a heterogeneous phase then being produced in a second stirred reactor.

2. Process according to claim 1, characterised in that an initial nitration ratio of between 4 and 8, and preferably between 5 and 7, is used.

3. Process according to claim 1 or 2, characterised in that a temperature of between 25° and 50° C., and preferably between 30° and 40° C., is caused to prevail in the first reactor, and a temperature of between 45° and 70° C., and preferably between 50° and 65° C., is caused to prevail in the second reactor.

4. Process according to claim 1 or 2, characterised in that the first two reactors in a cascade are followed by at least one third stirred reactor in which the temperature of the reaction mixture is brought back to about ambient temperature.

* * * * *